(12) United States Patent
Viens et al.

(10) Patent No.: US 10,532,123 B2
(45) Date of Patent: Jan. 14, 2020

(54) HYDROENTANGLED FIBROUS STRUCTURES

(71) Applicant: The Procter & Gamble Company, Cincinnati, OH (US)

(72) Inventors: Gerard A. Viens, Wyoming, OH (US); Christine R. Dodge, Liberty Township, OH (US); Matthias Hunnius, Frankfurt (DE)

(73) Assignee: The Procter & Gamble Company, Cincinnati, OH (US)

( * ) Notice: Subject to any disclaimer, the term of this patent is extended or adjusted under 35 U.S.C. 154(b) by 19 days.

(21) Appl. No.: 14/278,481

(22) Filed: May 15, 2014

(65) Prior Publication Data

US 2014/0343523 A1    Nov. 20, 2014

Related U.S. Application Data

(60) Provisional application No. 61/824,431, filed on May 17, 2013.

(51) Int. Cl.

| | |
|---|---|
| *A61F 13/537* | (2006.01) |
| *D04H 1/4258* | (2012.01) |
| *D04H 1/435* | (2012.01) |
| *D04H 1/541* | (2012.01) |
| *A61L 15/22* | (2006.01) |
| *D04H 1/498* | (2012.01) |

(52) U.S. Cl.
CPC ............ *A61L 15/225* (2013.01); *D04H 1/498* (2013.01)

(58) Field of Classification Search
CPC ............ A61F 13/53747; A61F 13/5376; A61F 13/5116; A61F 13/513; A61F 13/4702; A61F 2013/15983; A61F 2013/15357; A61F 2013/15406; A61F 2013/51028; A61F 2013/5104; A61F 2013/51057; A61F 13/511; A61F 13/537; D04H 1/4258; D04H 1/435; D04H 1/465; D04H 1/541

See application file for complete search history.

(56) References Cited

U.S. PATENT DOCUMENTS

| | | | |
|---|---|---|---|
| 4,321,924 A | 3/1982 | Ahr | |
| 4,425,130 A | 1/1984 | DesMarais | |
| 4,589,876 A | 5/1986 | Tilburg | |
| 4,950,264 A | 8/1990 | Osborn | |
| 5,607,414 A * | 3/1997 | Richards | ........... A61F 13/15203 604/358 |
| 5,810,796 A * | 9/1998 | Kimura | ............. A61F 13/15203 604/365 |
| 5,997,980 A * | 12/1999 | Matoba | .................... D01D 5/24 428/376 |

(Continued)

FOREIGN PATENT DOCUMENTS

| | | |
|---|---|---|
| EP | 2692321 | 2/2014 |
| JP | H10273884 | 10/1998 |
| JP | 2008106383 | 5/2008 |

OTHER PUBLICATIONS

PCT International Search Report, dated Nov. 17, 2015, 7 pages.

*Primary Examiner* — Peter S Vasat
(74) *Attorney, Agent, or Firm* — George H. Leal; Andrew J. Hagerty; Dara M. Kendall (57) ABSTRACT

A hydroentangled fibrous structure. The hydroentangled fibrous structure can be incorporated into an absorbent article. Methods of forming a hydroentangled fibrous structure are also provided.

18 Claims, 2 Drawing Sheets

(56) References Cited

U.S. PATENT DOCUMENTS

| | | | |
|---|---|---|---|
| 6,566,578 B1 | 5/2003 | Glaug et al. | |
| 7,597,689 B2* | 10/2009 | Hoffmann | A61F 13/495 604/378 |
| 8,389,427 B2 | 3/2013 | Gustafsson et al. | |
| 2003/0220048 A1* | 11/2003 | Toro | A61F 13/51462 450/57 |
| 2004/0087924 A1* | 5/2004 | Sroda | A61F 13/47209 604/367 |
| 2005/0033253 A1* | 2/2005 | Fuchs | A61F 13/53747 604/367 |
| 2006/0058762 A1* | 3/2006 | Yang | A61F 13/15203 604/380 |

* cited by examiner

HYDROENTANGLED FIBROUS STRUCTURES

TECHNICAL FIELD

The present disclosure generally relates to hydroentangled fibrous structures having improved performance characteristics, including flexural rigidity and fluid handling properties.

BACKGROUND

Disposable absorbent articles such as feminine hygiene products are designed to absorb fluids from the wearer's body. Users of feminine hygiene products have several concerns. Leakage from products like catamenial pads, and in particular sanitary napkins, is a significant concern. The feel of the product against the wearer's body is also a concern. To provide better comfort, current sanitary napkin products are typically provided with a topsheet that is flexible, soft feeling, and non-irritating to the wearer's skin. The topsheet does not itself hold the discharged fluid. Instead, the topsheet is fluid-permeable to allow the fluids to flow into an absorbent core.

Over the years, topsheets have improved to provide a cleaner, drier, and more comfortable in-use experience. In some feminine hygiene products, the topsheet is made of a hydrophobic material. These materials can include phobic nonwovens, hi-loft nonwovens, and softer films with significant texture (micro apertures, nubs that can trap fluid within the film structure etc.), and can be manufactured from a wide range of materials such as apertured plastic films, natural fibers (e.g., wood or cotton fibers), synthetic fibers (e.g., polyester or polypropylene fibers) or from a combination of natural and synthetic fibers. The hydrophobic nature of these materials helps to isolate the wearer's skin from liquids absorbed by the product and thus improves comfort by reducing the phenomenon known as "rewet".

Absorbent cores are well known in the art, and have conventionally included tangled masses of fibers, i.e., fibrous webs that can imbibe fluids both by an absorption mechanism (in which fluid is taken up by the fiber material itself) and by a wicking mechanism (in which fluid is acquired by, distributed through, and stored in capillary interstices between fibers).

Although the properties of a hydrophobic nonwoven topsheet helps to keep fluids in the core, the tendency of such topsheets to repel fluid creates a risk that the fluid will flow off the topsheet, rather than flow through the topsheet and into the absorbent core. This challenge is particularly evident in connection with feminine hygiene products, which commonly encounter fluid flow rates of less than 1-3 grams per hour, rather than the gushing flow rates commonly encountered by incontinence products. For fluid to flow into a feminine hygiene product, it must overcome not only the hydrophobic properties of the topsheet, but also the natural adhesion of the fluid to bodily surfaces.

To help ensure that fluids flow into the absorbent core, some feminine hygiene products with hydrophobic topsheets are constructed with what is sometimes referred to as a secondary topsheet (STS) directly beneath the topsheet. This secondary topsheet is designed to acquire the fluid on a liquid-permeable topsheet and distribute it to the underlying absorbent core. To help ensure that the secondary topsheet transfers the fluid to the absorbent core, secondary topsheets typically have sufficient capillarity to draw the fluid through the topsheet. To ensure that the fluid flow continues onto the absorbent core, the secondary topsheet is commonly designed with more permeability than the absorbent core, and less capillarity than the absorbent core.

Secondary topsheets are typically made from an airlaid-tissue web made from hydrophilic cellulosic fibers, sometimes referred to as an airlaid STS. Such secondary topsheets, however, cannot be fusion bonded to the topsheet due to the use of plain cellulosic fibers in the web. Accordingly, glue is used during the manufacturing process as a bonding agent between the airlaid STS and the topsheet. If fusion bonding is desired, a polyethylene (PE) powder can be incorporated into the airlaid STS, but a sufficiently high basis weight is required, which may be undesirable.

Accordingly, it would be desirable to provide a fibrous web for use as a secondary topsheet, with the fibrous web having a relatively lower basis weight, while still having a sufficient flexural rigidity and desired fluid handling and performance characteristics.

SUMMARY

In accordance with one embodiment, a hydroentangled fibrous structure has a basis weight between about 35 grams per square meter (gsm) and about 65 gsm, a machine direction (MD) bending stiffness of about 0.2 mN·cm to about 7 mN·cm, and a rewet value of about 0.2 g to about 7.0 g.

In accordance with another embodiment, a hydroentangled fibrous structure includes about 30% to about 60%, by weight, of cellulosic fibers, about 5% to about 30%, by weight, of non-cellulosic fibers, and about 30% to about 55%, by weight, of polyolefin-based binder fibers.

In accordance with yet another embodiment, an absorbent article includes a topsheet, an absorbent core, and a secondary topsheet positioned between the topsheet and the absorbent core, where the secondary topsheet includes a hydroentangled fibrous structure having a basis weight of about 35 grams per square meter (gsm) to about 65 gsm, a machine direction (MD) bending stiffness of about 0.2 mN·cm to about 7 mN·cm, and a rewet value of about 0.2 g to about 7.0 g.

In accordance with still yet another embodiment, a disposable absorbent article includes a topsheet, an absorbent core, and a hydroentangled secondary topsheet positioned between the topsheet and the absorbent core. The topsheet, the absorbent core, and the hydroentangled secondary topsheet cooperate to provide excellent acquisition rate and rewet properties.

In accordance with another embodiment, a nonwoven web is prepared by a process. The process includes hydroentangling a fibrous structure, the fibrous structure including a first fibrous component, a second fibrous component, and a third fibrous component, where the third fibrous component is formed from bicomponent fibers including a first material and a second material, where the first material of the bicomponent fiber has a softening temperature lower than a softening temperature of the second material. The process also includes substantially drying the hydroentangled fibrous structure to remove moisture and heating the substantially dried hydroentangled fibrous structure to a temperature to stiffen the fibrous structure, where the temperature is higher than the softening temperature of the first material and lower than the softening temperature of the second material.

While the specification concludes with claims particularly pointing out and distinctly claiming the subject matter that is regarded as the present invention, it is believed that the invention will be more fully understood from the following description taken in conjunction with the accompanying drawings. Some of the figures may have been simplified by the omission of selected elements for the purpose of more clearly showing other elements. Such omissions of elements in some figures are not necessarily indicative of the presence or absence of particular elements in any of the exemplary embodiments, except as may be explicitly delineated in the corresponding written description. None of the drawings are necessarily to scale.

DETAILED DESCRIPTION

As used herein, the following terms shall have the meaning specified thereafter:

"Absorbent article" refers to wearable devices, which absorb and/or contain liquid, and more specifically, refers to devices, which are placed against or in proximity to the body of the wearer to absorb and contain the various exudates discharged from the body. Absorbent articles can include diapers, training pants, adult incontinence undergarments, feminine hygiene products.

The "longitudinal" direction is a direction running parallel to the maximum linear dimension, typically the longitudinal axis, of the article and includes directions within 45° of the longitudinal direction. "Length" of the article or component thereof, when used herein, generally refers to the size/distance of the maximum linear dimension, or typically to the size/distance of the longitudinal axis, of an article or part thereof.

The "lateral" or "transverse" direction is orthogonal to the longitudinal direction, i.e. in the same plane of the majority of the article and the longitudinal axis, and the transverse direction is parallel to the transverse axis. "Width" of the article or of a component thereof, when used herein, refers to the size/distance of the dimension orthogonal to the longitudinal direction of the article or component thereof, i.e. orthogonal to the length of the article or component thereof, and typically it refers to the distance/size of the dimension parallel of the transverse axis of the article or component.

The "Z-direction" is orthogonal to both the longitudinal and transverse directions.

"Machine Direction" or "MD" as used herein means the direction parallel to the flow of the hydroentangled fibrous structure through the hydroentangled fibrous structure making machine and/or absorbent article product manufacturing equipment.

"Cross Machine Direction" or "CD" as used herein means the direction parallel to the width of the hydroentangled fibrous structure making machine and/or absorbent article product manufacturing equipment and perpendicular to the machine direction.

"Disposable" is used herein to describe articles that are generally not intended to be laundered or otherwise restored or reused (i.e., they are intended to be discarded after a single use and, may be recycled, composted or otherwise disposed of in an environmentally compatible manner).

"Absorbent core" refers to a structure typically disposed between a topsheet and backsheet of an absorbent article for absorbing and containing liquid received by the absorbent article. The absorbent core may comprise one or more substrate layer, absorbent material disposed on the one or more substrate layer, and a thermoplastic adhesive composition on the absorbent material. The thermoplastic adhesive composition may be on the absorbent material and at least a portion of the one or more substrate layer. The absorbent core does not include an acquisition system, a topsheet, or a backsheet of the absorbent article. In a certain embodiment, the absorbent core would consist essentially of the one or more substrate layers, the absorbent material, the thermoplastic adhesive composition, and optionally a cover layer.

"Nonwoven material" refers to a manufactured web of directionally or randomly orientated fibers, excluding paper and products which are woven, knitted, tufted, stitch-bonded incorporating binding yarns or filaments, or felted by wet-milling, whether or not additionally needled. Nonwoven materials and processes for making them are known in the art. Generally, processes for making nonwoven materials comprise laying fibers onto a forming surface, which can comprise spunlaying, meltblowing, carding, airlaying, wet-laying, coform and combinations thereof. The fibers can be of natural or man-made origin and may be staple fibers or continuous filaments or be formed in situ.

The term "hydrophilic" describes fibers or surfaces of fibers, which are wettable by aqueous fluids (e.g., aqueous body fluids) deposited on these fibers. Hydrophilicity and wettability are typically defined in terms of contact angle and the strike-through time of the fluids, for example through a nonwoven fabric. This is discussed in detail in the American Chemical Society publication entitled "Contact Angle, Wettability and Adhesion", edited by Robert F. Gould (Copyright 1964). A fiber or surface of a fiber is said to be wetted by a fluid (i.e., hydrophilic) when either the contact angle between the fluid and the fiber, or its surface, is less than 90°, or when the fluid tends to spread spontaneously across the surface of the fiber, both conditions are normally co-existing. Conversely, a fiber or surface of the fiber is considered to be "hydrophobic" if the contact angle is greater than 90° and the fluid does not spread spontaneously across the surface of the fiber.

As used herein, the term "comprising" means that the various components, ingredients, or steps can be conjointly employed in practicing the present invention. Accordingly, the term "comprising" is open-ended and encompasses the more restrictive terms "consisting essentially of" and "consisting of".

A hydroentangled fibrous structure as disclosed herein can be used in a variety of disposable absorbent articles, but is particularly useful in feminine hygiene products such as sanitary napkins, pantiliners, and incontinence pads. One embodiment of a disposable absorbent article that incorporates a hydroentangled fibrous structure is shown as a sanitary napkin in FIGS. 1 and 2.

Figure 1:
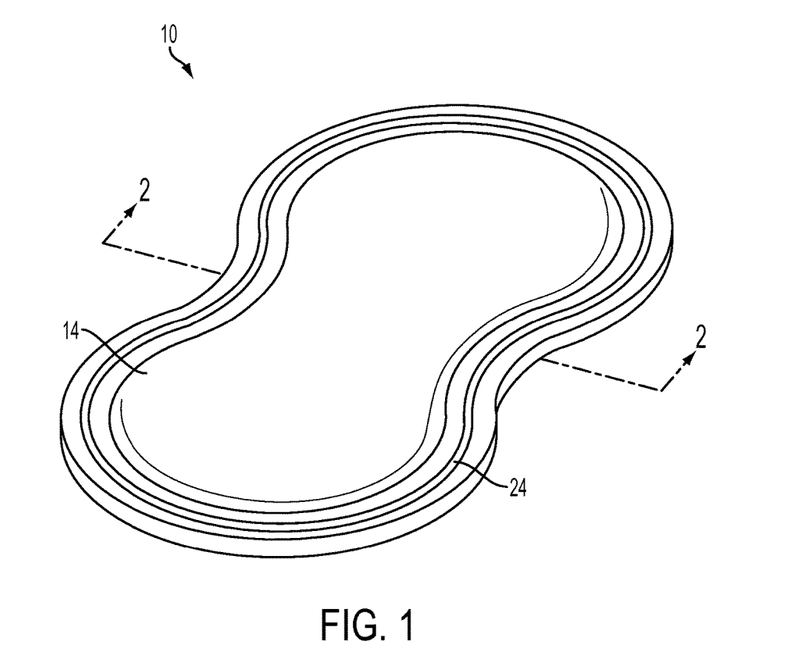
FIG. 1 is a perspective view of one example of a sanitary napkin that incorporates a hydroentangled secondary topsheet.

A sanitary napkin 10 can have any shape known in the art for feminine hygiene articles, including the generally symmetric "hourglass" shape as shown in FIG. 1, as well as pear shapes, bicycle-seat shapes, trapezoidal shapes, wedge shapes or other shapes that have one end wider than the other. Sanitary napkins and pantiliners can also be provided with lateral extensions known in the art as "flaps" or "wings" (not shown in FIG. 1). Such extensions can serve a number of purposes, including, but not limited to, protecting the wearer's panties from soiling and keeping the sanitary napkin secured in place. The illustrated absorbent article has a body-facing upper side that contacts the user's body during use. The opposite, garment-facing lower side contacts the user's clothing during use.

The upper side of the sanitary napkin 10 generally has a topsheet 14 that can be liquid pervious. The lower side (seen in FIG. 2) has a backsheet 16 that can generally be liquid impervious and is joined with the topsheet 14 at the edges 12 of the sanitary napkin 10. An absorbent core 18 is positioned between the topsheet 14 and the backsheet 16.

Figure 2:
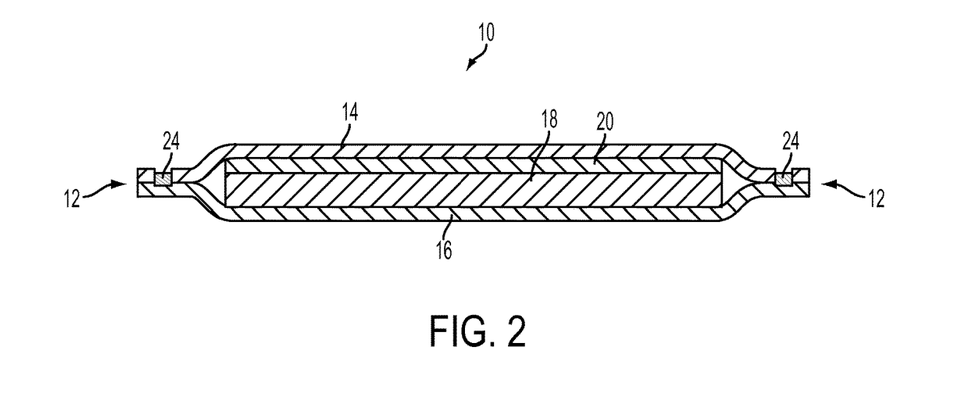
FIG. 2 is a cross-sectional view of the sanitary napkin of FIG. 1, taken through line 2-2.

A secondary topsheet 20 can be provided at the top of the absorbent core 18, beneath the topsheet 14. As described in more detail below, the secondary topsheet 20 can include a hydroentangled fibrous structure manufactured in accordance with the present disclosure. The topsheet 14, the backsheet 16, and the absorbent core 18 can be assembled in a variety of well-known configurations, including so called "tube" products or side flap products. Example sanitary napkin configurations are described generally in U.S. Pat. No. 4,950,264, "Thin, Flexible Sanitary napkin" issued to Osborn on Aug. 21, 1990, U.S. Pat. No. 4,425,130, "Compound Sanitary napkin" issued to DesMarais on Jan. 10, 1984; U.S. Pat. No. 4,321,924, "Bordered Disposable Absorbent Article" issued to Ahr on Mar. 30, 1982; U.S. Pat. No. 4,589,876, and "Shaped Sanitary napkin With Flaps" issued to Van Tilburg on Aug. 18, 1987.

The backsheet 16 and the topsheet 14, as shown in FIGS. 1 and 2, can be secured together in a variety of ways. Adhesives manufactured by H. B. Fuller Company of St. Paul, Minn. under the designation HL-1258 or H-2031 have been found to be satisfactory. Alternatively, the topsheet 14 and the backsheet 16 can be joined to each other by heat bonding, pressure bonding, ultrasonic bonding, dynamic mechanical bonding, a crimp seal, or by any other suitable securing method. As shown in FIG. 2, a fluid impermeable crimp seal 24 can resist lateral migration ("wicking") of fluid through the edges of the product, inhibiting side soiling of the wearer's undergarments.

As is typical for sanitary napkins and the like, the sanitary napkin 10 of the present disclosure can have panty-fastening adhesive disposed on the garment-facing side of backsheet 16. The panty-fastening adhesive can be any of known adhesives used in the art for this purpose, and can be covered prior to use by a release paper, as is well known in the art. If flaps or wings are present, a panty fastening adhesive can be applied to the garment facing side so as to contact and adhere to the underside of the wearer's panties.

To provide for softness next to the body, the topsheet 14 of the illustrated sanitary napkin 10 can be formed from a soft, smooth, flexible, porous material that is non-irritating to the user's skin. The topsheet 14 is permeable to the body fluids to be collected by the article and thus, for a sanitary napkin, is permeable to vaginal discharges. Generally, topsheets for absorbent articles can be made from a wide range of materials such as woven and nonwoven materials; polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be comprised of natural fibers (e.g., wood or cotton fibers), synthetic fibers (e.g., polymeric fibers such as polyester, polypropylene, or polyethylene fibers) or from a combination of natural and synthetic fibers.

Hydrophobic topsheets have a reduced tendency to allow fluids to pass back through and rewet the wearer's skin. Thus, the surface of the formed film (or nonwoven) that is in contact with the body remains dry, thereby reducing body soiling and creating a more comfortable feel for the wearer.

Example topsheets are hydrophobic topsheets selected from typical nonwoven forming approaches such as spunbonded, carded, hydroentangled, needled, through-air bonded, or high loft nonwoven topsheets, and apertured 2-dimensional or 3-dimensional film topsheets. Lofty apertured formed film topsheets, with appreciable topsheet texture (nubs, micro-texture or with filament-like protrusions on the body-facing surface that can trap bodily discharges and hinder low fluid flows towards the body) that may be hydrophobic or hydrophilic in nature, can also be used. Apertured formed films are especially preferred for the topsheet 14 because they are pervious to body exudates and non-absorbent.

Still referring to FIG. 1, the absorbent core 18 of a sanitary napkin serves to store bodily fluids discharged during use. The absorbent core 18 can be manufactured in a wide variety of sizes and shapes, and may be profiled to have different thickness, hydrophilic gradients, superabsorbent gradients, densities, or average basis weights at different positions across the face of the sanitary napkin 10.

The absorbent core 18 can have a fluid distribution layer as well as a fluid storage layer. The fluid distribution layer transfers received fluid both downwardly and laterally, and generally has more permeability and less capillarity than the fluid storage layer.

In addition to conventional absorbent materials such as creped cellulose wadding, fluffed cellulose fibers, wood pulp fibers also known as airfelt, and textile fibers, the fluid storage layer often includes superabsorbent material that imbide fluids and form hydrogels. These materials are typically capable of absorbing large quantities of body fluids and retaining them under moderate pressures. The fluid storage layer of the absorbent core 18 can be made solely of superabsorbent material, or can include such materials dispersed in a suitable carrier such as cellulose fibers in the form of fluff or stiffened fibers. Synthetic fibers including cellulose acetate, polyvinyl fluoride, polyvinylidene chloride, acrylics (such as ORLON), polyvinyl acetate, non-soluble polyvinyl alcohol, polyethylene, polypropylene, polyamides (such as nylon), polyesters, bicomponent fibers, tricomponent fibers, mixtures thereof and the like can also be used. The fluid storage layer can also include filler materials, such as PERLITE, diatomaceous earth, VERMICULITE, or other suitable materials, that lower rewet problems.

However structured, the total absorbent capacity of the absorbent core 18 should be compatible with the design loading and the intended use of the article (e.g., sanitary napkin 10). Thus, the size and absorbent capacity of the absorbent core 18 can be varied to accommodate different uses such as incontinence pads, pantiliners, regular sanitary napkins, or overnight sanitary napkins.

The backsheet 16 that covers the lower side of the absorbent core 18 prevents the fluids in the absorbent core 18 from wetting articles that contact the sanitary napkin 20, such as pants, pajamas and undergarments. Accordingly, the backsheet 16 is preferably made from a liquid impervious thin film or a liquid impervious but vapor pervious film/nonwoven laminate, a microporous film, an apertured formed film, or other polymer film that is vapor permeable, or rendered to be vapor permeable, but substantially impervious to fluid.

The secondary topsheet 20 is interposed between the absorbent core 18 and the topsheet 14, and serves to rapidly draw discharged body fluids, in particular menstrual fluids, through the adjacent permeable (primary) topsheet 14. This allows the surface of the primary topsheet 14 adjacent the wearer of the article to remain relatively clean and dry. The secondary topsheet 20 in the illustrated sanitary napkin 10 has a hydroentangled (i.e., spunlaced) fibrous web or matrix that is comprised of a plurality of fiber types.

Included in the hydroentangled fibrous web can be a cellulosic fibrous component, a non-cellulosic fibrous component, and a polyolefin-based binder fibrous component. The polyolefin-based binder fibrous component can be a bicomponent fiber. As used hereinafter the term bicomponent fibers refers to fibers having two constituents. Typically, bicomponent fibers are constituted of relatively similar constituents, which are differing, for example in their melting temperature or softening temperature. Some hydroentangled fibrous structures manufactured in accordance with the present disclosure are polypropylene/polyethylene bicomponent fibers. Other combinations, such as polyester/polyethylene, polyester/polypropylene, polyamide/polyester, polyamide/polyethylene, polyamide/polypropylene, are also feasible combinations.

The bicomponent fibers can have any cross-section type, such as side-by-side, concentric or eccentric. As used herein, the term "side-by-side" refers to fibers having two components divided along the length into two or more distinct regions. As used herein, the terms "concentric" and "eccentric" refer to whether a sheath of the bicomponent fibers has a thickness that is even, or uneven, through the cross-sectional area of the bicomponent fiber. Eccentric bicomponent fibers can be desirable in providing more compressive strength at lower fiber thicknesses. Suitable bicomponent fibers for use herein can be either uncrimped (i.e. unbent) or crimped (i.e. bent). Bicomponent fibers can be crimped by typical textile means such as, for example, a stuffer box method or the gear crimp method to achieve a predominantly two-dimensional or "flat" crimp.

Generally, the secondary topsheet 20 manufactured with a hydroentangled fibrous structure in accordance with the present disclosure provides capillary suction to "pull" fluid through the topsheet 14, which is competing for trickle/low flow conditions. The secondary topsheet 20 also can contain a gush by providing permeability for movement of fluid to the absorbent core 18, as well as provide intermediate storage until the absorbent core 18 can accept fluid.

The secondary topsheet 20 can also provide stiffness and flexural rigidity which is generally required to prevent, or at least attempt to reduce, cross machine direction (CD) bunching while maintaining comfort and body fit. The hydroentangled fibrous web of the secondary topsheet 20 can have a basis weight of 90 grams per square meter (gsm) or less; or a basis weight of 65 gsm or less; or a basis weight in the range of about 35 gsm to about 65 gsm; or in the range of about 45 gsm to about 60 gsm; or in the range of about 50 gsm to about 55 gsm. The hydroentangled fibrous structure of the secondary topsheet 20 can also have a machine direction (MD) bending stiffness of about 0.2 mN·cm to about 12 mN·cm. In some embodiments, the hydroentangled fibrous structure has a MD bending stiffness of about 1.0 mN·cm to about 7 mN·cm, The hydroentangled fibrous structure of the secondary topsheet 20 can be manufactured from an assortment of suitable fiber types that produce the desired mechanical performance and fluid handling performance. The cellulosic fibrous component, for example, can form about 30% to about 60%, by weight, of the hydroentangled fibrous structure. For some example secondary topsheets, the cellulosic fibrous component can form about 35% to 55%, by weight, of the hydroentangled fibrous structure. In other embodiments, the cellulosic fibrous component can form about 36% to 45%, by weight, of the hydroentangled fibrous structure. Furthermore, the cellulosic fibers of the hydroentangled fibrous structure can be hydrophilic.

The cellulosic fibrous can be rayon, such as viscose rayon, or other suitable cellulosic fibers known in the art, such as cotton. For hydroentangled fibrous structures including rayon, the rayon can have a decitex (dtex) in the range of about 1.3 to about 7.0. Some hydroentangled fibrous structures can include rayon having a dtex in the range of about 1.5 to about 1.9. The staple length of the rayon can be in the range of about 30 mm to about 75 mm or about 35 mm to about 45 mm.

The non-cellulosic, or synthetic, fibrous component can form about 5% to about 70%, by weight, of the hydroentangled fibrous structure of the secondary topsheet 20. For some example secondary topsheets, the non-cellulosic fibrous component can form about 10% to 25%, by weight, of the hydroentangled fibrous structure. Yet other example secondary topsheets can include a hydroentangled fibrous structure that is formed with about 15% to 24%, by weight, of the non-cellulosic fibrous component.

The non-cellulosic fibrous can be polyethylene terephthalate (PET) fibers, or other suitable non-cellulosic fibers known in the art. For hydroentangled fibrous structures including PET fibers, the PET fibers can have a dtex in the range of about 3.5 to about 12.0. Some hydroentangled fibrous structures can include PET fibers having a dtex in the range of about 3.8 to about 5.1. While other hydroentangled fibrous structures can include PET fibers having a dtex in the range of about 4.1 to about 4.7. The staple length of the PET fibers can be in the range of about 28 mm to about 48 mm or about 37 mm to about 43 mm. Some hydroentangled fibrous structures include PET fibers with a staple length of about 38 mm to 42 mm. The PET fibers can have any suitable structure or shape. For example, the PET fibers can be round or have other shapes, such as spiral, scalloped oval, trilobal, scalloped ribbon, and so forth. Further, the PET fibers can be solid, hollow or multi-hollow. The bicomponent fibrous component, sometimes referred to as a polyolefin-based binder fibrous component, can form about 30% to about 55%, by weight, of the hydroentangled fibrous structure. For some example secondary topsheets, the bicomponent fibrous component forms about 35% to 50%, by weight, of the hydroentangled fibrous structure. Yet other hydroentangled fibrous structures can be formed by about 36% to 45%, by weight, of the bicomponent fibrous component.

With specific reference to bicomponent fibers comprised of a polypropylene/polyethylene fiber composition, in a cross-sectional view of a fiber, the material with a higher softening temperature can provide the central part (i.e., the core) of the fiber. The core typically is responsible for the bicomponent fiber's ability to transmit forces and have a certain rigidity or otherwise provide structures with resiliency. The outer coating on the core (i.e., the sheath) of the fiber can have a lower melting point and is used to facilitate thermally bonding of substrates comprising such fibers. In one embodiment, a polypropylene core is provided with a polyethylene coating on the outside, such that about 50%, by weight, of the fiber material is polypropylene and 50%, by weight, of the fiber material is polyethylene. Other quantitative amounts can of course be selected. For example, bicomponent fibers can have a composition from about 30% to about 70%, by weight, polyethylene, while others have about 35% to about 65%, by weigh polyethylene. In some embodiments, bicomponent fibers can have a composition from about 40% to about 60% or about 45% to about 55%, by weight, polyethylene.

The hydroentangled fibrous structure of the secondary topsheet 20 formed in accordance with the present disclosure imparts a number of desirable physical properties, including its wicking/capillarity, wet Z-direction crush resistance, flexural rigidity, as well as the ability to fusion bond to a film or nonwoven topsheet (i.e., topsheet 14). Generally, the cellulosic fibrous component of the hydroentangled fibrous structure, such as rayon, provides capillarity which serves to transport fluid from the topsheet 14 to the absorbent core 18. The non-cellulosic fibrous component of the hydroentangled fibrous structure, such as PET, provides Z-direction strength to prevent, or at least limit, collapse of the secondary topsheet 20 when wetted while also providing desirable permeability. The polyolefin-based fibrous component of the hydroentangled fibrous structure, such as polypropylene/polyethylene fibers, serve to provide capillarity while also allowing the secondary topsheet 20 to be bonded to the topsheet 14 and to each other to increase the stiffness of the secondary topsheet 20 to desired levels.

Methods of Making Hydroentangled Fibrous Structures

Figure 3:
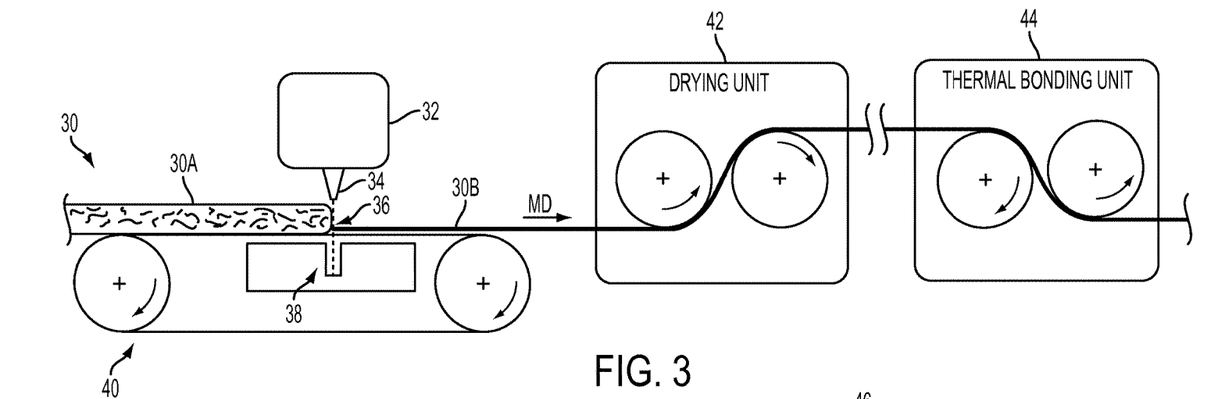
FIG. 3 depicts a simplified, schematic view of one example continuous hydroentangled fibrous structure manufacturing process.

FIG. 3 depicts a simplified, schematic view of one example continuous hydroentangled fibrous structure manufacturing process. As is to be appreciated, the hydroentangled fibrous structure produced by the process of FIG. 3 can be used in the manufacturing of a variety of absorbent articles, such as the sanitary napkin 10 of FIGS. 1-2, as well as a variety of other absorbent articles, including diapers, training pants, adult incontinence undergarments, and the like.

As is generally known in the art, hydroentanglement (sometimes referred to as spunlacing, jet entanglement, water entanglement, hydroentanglement or hydraulic needling), is a mechanical bonding process whereby fibers of a nonwoven web are entangled by means of high pressure water jets. Patterning can be achieved by use of patterned drums or belts which cause the fibers to form a negative image of the drum design in the fabric. The formed web of various fibrous components (usually airlaid, wetlaid, or carded, but sometimes spunbond or melt-blown, etc.) can first be compacted and prewetted to eliminate air pockets and then water-needled. With reference to FIG. 3, a fibrous structure 30 is formed from cellulosic fibers, non-cellulosic fibers and bicomponent fibers. The fibrous structure 30 has an unbonded portion 30A upstream of a jet head 32 and a bonded (i.e., hydroentangled) portion 30B downstream of the jet head 32. During the entanglement process, the fibrous structure 30 is passed by the jet head 32 that comprises a plurality of injectors that are positioned to generally form a water curtain (for simplicity of illustration, only one injector 34 is illustrated in FIG. 3). A water jet 36 is directed through the fibrous structure 30 at high pressures, such as 150 or 400 bar. As is to be appreciated, while not illustrated, multiple rows of injectors 34 are typically used, which can be positioned on one or both sides of the fibrous structure 30.

The fibrous structure 30 can be supported by any suitable support system 40, such as a moving wire screen (as illustrated) or on a rotating porous drum, for example. While not illustrated, it is to be appreciated that hydroentanglement systems can expose the fibrous structure 30 to a series of jet heads 32 along the machine direction, with each delivering water jets at different pressures. The particular number of jet heads 32 utilized can be based on, for example, desired basis weight, degree of bonding required, characteristics of the web, and so forth. As the water jet 36 penetrates the web, a suction slot 38 positioned proximate beneath the fibrous structure 30 collects the water so that it can be filtered and returned to the jet head 32 for subsequent injection. The water jet 36 delivered by the jet head 32 exhausts most of its kinetic energy primarily in rearranging fibers within the fibrous structure 30 to turn and twist the fibers to form a series of interlocking knots.

Once the fibrous structure 30 has been hydroentangled (shown as bonded portion 30B), the hydroentangled fibrous structure 30 is then passed through a dewatering device where excess water is removed. In the process illustrated in FIG. 3, the dewatering device is a drying unit 42. The drying unit 42 can be any suitable drying system, such as a multi-segment multi-level bed dryer, a vacuum system, and/or an air drum dryer, for example. The drying unit 42, or other dewatering device, serves to substantially dry the hydroentangled fibrous structure 30 before subsequent heat treatment. The term "substantially dry" is used herein to mean that the hydroentangled fibrous structure 30 has a liquid content, typically water or other solution content, less than about 10%, less than about 5%, or less than about 3%, by weight.

Once the hydroentangled fibrous structure 30 is substantially dry, the hydroentangled fibrous structure 30 can be heated to an elevated temperature. By heating the hydroentangled fibrous structure 30 to a particular temperature, or temperature range, the flexural rigidity of the fibrous structure can be increased (i.e., stiffened). Stiffening the fibrous structure results in a number of desired results. For example, the increase of stiffness of the hydroentangled fibrous structure 30 allows the structure to tolerate the subsequent manufacturing processes. Additionally, when the hydroentangled fibrous structure 30 is subsequently incorporated into an absorbent article, such as sanitary napkin 10, for example, cross machine direction (CD) bunching is reduced, leading to less leakage and more comfort for a wearer.

By introducing additional heat to the hydroentangled fibrous structure 30 to raise its temperature during the thermal bonding process, the sheath of the bicomponent fibers will first begin to soften. As these softened bicomponent fibers touch each other, bonds will form between the sheaths, thereby increasing the overall flexural rigidity of the structure due to the formation of these bond sites. The elevated temperature of the hydroentangled fibrous structure 30 is not high enough, however, to cause other types of fibers within the hydroentangled fibrous structure to flow or otherwise soften, bond, or collapse. The formation of the bond sites within the hydroentangled fibrous structure 30 adds to the stiffness of the web, yet the fluid handling performance of the hydroentangled fibrous structure 30 remains as desired. It will be recognized that raising the final drying stage temperature (or otherwise introducing heat to the hydroentangled fibrous structure) to just above a softening temperature of a portion of the bicomponent fiber provides an increase in mechanical performance while also maintaining liquid handling performance. If, however, the hydroentangled fibrous structure is heated to too high of temperature, the rigidity of the structure increases and the liquid handling performance of the structure can suffer.

In order to elevate the temperature, the substantially dry hydroentangled fibrous structure 30 can be passed to another heating unit (schematically shown as a thermal bonding unit 44 in FIG. 3). In other embodiments, the hydroentangled fibrous structure 30 is wound subsequent to being substantially dried by the drying unit 42. At a later point in time, perhaps after being transported to another facility, the hydroentangled fibrous structure 30 is unwound and then heat stiffened using a thermal bonding unit 44. At that point, the heat stiffened hydroentangled fibrous structure can either be wound again for later processing or it can be incorporated into an absorbent article or product downstream of the thermal bonding unit 44.

Figure 4:
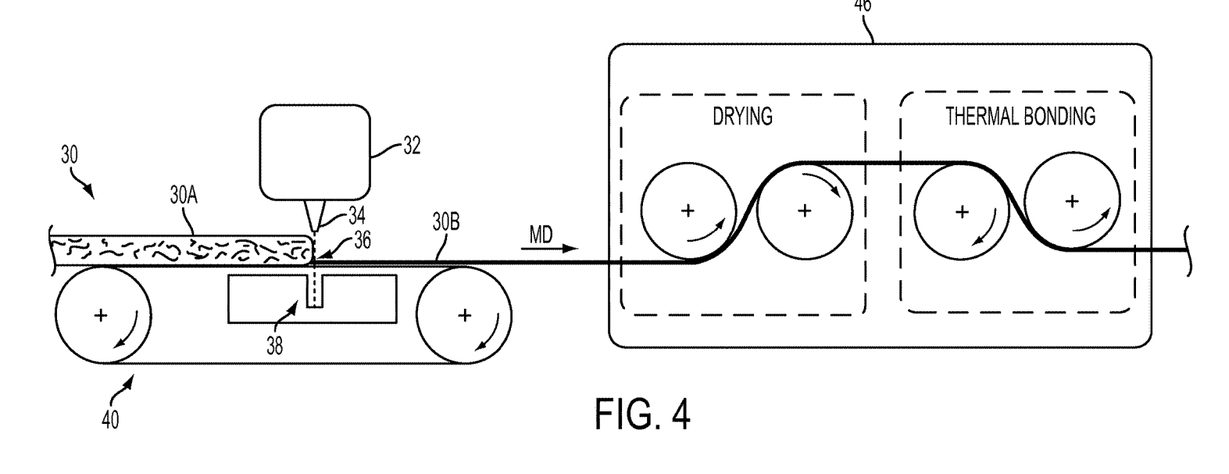
FIG. 4 depicts a simplified, schematic view of another example continuous hydroentangled fibrous structure manufacturing process.

Referring now to FIG. 4, in one example embodiment, the drying of the fibrous structure 30 and the subsequent thermal bonding of the hydroentangled fibrous structure 30 are performed within a single drying system, illustrated as heating unit 46, which can be a conventional oven or dryer used during spunlace manufacturing processes. The heating unit 46 can deliver various levels of heat to the hydroentangled fibrous structure 30 in stages. The first stages are used to substantially dry the hydroentangled fibrous structure 30. During the final stages of the drying process within the heating unit 46, the temperature of the hydroentangled fibrous structure 30 is elevated such that at least a portion of the bicomponent materials soften and begin to bond to one another. While a multi-stage heating process is illustrated in FIG. 4, this disclosure is not so limited. For example, the hydroentangled fibrous structure 30 can be substantially dried and thermally bonding using a single-stage heating process. In one example process, the hydroentangled fibrous structure 30 is dewatered, substantially dried, and thermally melted using a single through-air drum drier.

Once the hydroentangled fibrous structure 30 is manufactured in accordance with the present disclosure it can be incorporated into, for example, an absorbent material. With regard to the sanitary napkin 10 of FIGS. 1-2, the secondary topsheet 20 incorporating the hydroentangled fibrous structure 30 can be bonded to, or otherwise attached to the topsheet 14. In some embodiments, thermal point calendaring or other suitable bonding is utilized. In other embodiments, the hydroentangled fibrous structure 30 can serve as an absorbent core of an absorbent article. For example, pantiliners and incontinence pads can be formed with the hydroentangled fibrous structure 30 positioned between a topsheet and a bottom sheet to function as an absorbent core, as described above with respect to FIGS. 1-2. Furthermore, in some embodiments, the hydroentangled fibrous structure 30 does not include a binder component. Test Methods Hydroentangled fibrous structure samples were produced having a basis weight of 55 gsm, with smooth surfaced and a homogeneous blend of (1) about 40% viscose rayon fibers (1.7 dtex, 38 mm staple length), (2) about 40% bicomponent fibers formed from polypropylene (PP) and polyethylene (PE) (1.7 dtex, 40 mm length, PE sheath 50% by weight and PP core 50% by weight), which includes about 1.0% titanium dioxide ($TiO_2$), and (3) about 20% polyethylene terephthalate (PET) (40 mm staple length). Unless otherwise specified, all tests described herein were conducted on samples conditioned at a temperature of 73° F.±4° F. (about 23° C.±2.2° C.) and a relative humidity of 50%±4% for 2 hours prior to the test. As illustrated below in Tables 1-5, elevating the temperature of the substantially dry hydroentangled fibrous structure samples to a certain temperature served to increase flexural rigidity (Table 1), while maintaining desirable fluid handling properties (Tables 2-5).

Table 1, below, illustrates example machine direction (MD) bending stiffness for the hydroentangled fibrous structure sample referenced above. The data provided in Table 1 was gathered in accordance with EDANA test method no. WSP 090.5 (Bending Length). The temperatures indicated in Table 1, as well as Tables 2, 3, 4, and 5, below, reflect the final drying stage temperature (i.e., the thermal bonding temperature) of the hydroentangled fibrous structure. As shown, raising the final drying stage temperature to just above the softening temperature (i.e., 131° C.), results in an approximately ten times increase in flexural rigidity while maintaining fluid handling performance. At a higher temperature, however, flexural rigidity continues to increase but fluid handling performance suffers:

TABLE 1

| | Temperature: 127° C. | Temperature: 131° C. | Temperature: 134° C. |
|---|---|---|---|
| MD Bending Stiffness (mN · cm) | 0.55 | 5.2 | 9.55 |

Table 2, below, illustrates example liquid strike through timing data for the hydroentangled fibrous structure sample referenced above. The data provided in Table 2 was gathered in accordance with EDANA test method no. WSP 070.7 (Repeated Liquid Strike-Through Time):

TABLE 2

| | Temperature: 127° C. | Temperature: 131° C. | Temperature: 134° C. |
|---|---|---|---|
| Strike Through 1 (sec.) | 1.5 | 1.7 | 3.05 |
| Strike Through 2 (sec.) | 3.5 | 3.72 | 4.3 |
| Strike Through 3 (sec.) | 3.3 | 3.5 | 3.66 |

Table 3, below, illustrates example rewet data for the hydroentangled fibrous structure sample referenced above. The data provided in Table 3 was gathered in accordance with EDANA test method no. WSP 080.10 (Coverstock Wetback):

TABLE 3

| | Temperature: 127° C. | Temperature: 131° C. | Temperature: 134° C. |
|---|---|---|---|
| Rewet (g) | 3.22 | 2.94 | 2.37 |

Table 4, below, illustrates example run off data for the hydroentangled fibrous structure sample referenced above. The data provided in Table 4 was gathered in accordance with EDANA test method no. WSP 080.9 (Run-Off):

TABLE 4

| | Temperature: 127° C. | Temperature: 131° C. | Temperature: 134° C. |
|---|---|---|---|
| Run Off (%) | 0 | 2.54 | 11.1 |

Table 5, below, illustrates example wicking data for the hydroentangled fibrous structure sample referenced above. The data provided in Table 5 was gathered in accordance with EDANA test method no. WSP 010.1 (Nonwoven Absorption):

TABLE 5

|  | Temperature: 127° C. | Temperature: 131° C. | Temperature: 134° C. |
|---|---|---|---|
| MD Wicking 120 sec (mm) | 29.3 | 3.2 | 9.3 |
| CD Wicking 120 sec (mm) | 19 | 3 | 3.5 |

Table 6, below, illustrates exemplary hydroentangled fibrous structures of the present invention, the structures having a basis weight of from about 45 gsm to about 85 gsm.

TABLE 6

|  | Viscose Rayon (wt %, dtex) | PET (wt %, dtex) | PE/PP Bico (wt %, dtex) |
|---|---|---|---|
| Example 1 | 60, 1.3 | 20, 4.4 | 20, 1.7 |
| Example 2 | 40, 1.3 | 20, 4.4 | 40, 1.7 |
| Example 3 | 40, 1.3 | 20, 4.4 | 40, 1.7 |
| Example 4 | 50, 1.3 | 20, 4.4 | 30, 1.7 |
| Example 5 | 60, 1.7 | 20, 4.4 | 20, 1.7 |
| Example 6 | 50, 1.7 | 20, 4.4 | 30, 1.7 |
| Example 7 | 50, 1.3 | 15, 4.4 | 35, 1.7 |
| Example 8 | 40, 1.7 | 20, 4.4 | 40, 1.7 |
| Example 9 | 50, 1.7 | 15, 4.4 | 35, 1.7 |

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article, comprising:
   a topsheet;
   an absorbent core; and
   a secondary topsheet positioned between the topsheet and the absorbent core, wherein the secondary topsheet comprises a hydroentangled fibrous structure having a basis weight of about 35 grams per square meter (gsm) to about 65 gsm, the hydroentangled fibrous structure comprising a substantially homogenous blend of fibers and having a thermally activated binder component to impart a machine direction (MD) bending stiffness of about 0.2 mN·cm to about 7 mN·cm according to EDANA test method number WSP 090.5; and
   wherein the blend of fibers comprises a first fibrous component; a second fibrous component, wherein said first fibrous component comprises cellulose fibers of 1.3 to 7.0 dtex, wherein said second fibrous component is a non-cellulosic fiber, said second fibrous component being from about 10% to about 25% by weight of the hydroentangled fibrous structure, and a third fibrous component, the third fibrous component defining the binder component and being formed from bicomponent fibers, said binder component being from about 36% to about 55% by weight of the hydroentangled fibrous structure.

2. The absorbent article of claim 1, wherein the bicomponent fibers comprise polyethylene.

3. The absorbent article of claim 1, wherein the first fibrous component comprises rayon and the second fibrous component comprises polyethylene terephthalate (PET).

4. The absorbent article of claim 1, wherein the bicomponent fibers form about 36% to about 46% by weight, of the hydroentangled fibrous structure.

5. The absorbent article of claim 1, wherein the secondary topsheet is bonded to the topsheet.

6. The absorbent article of claim 1, wherein hydroentangled fibrous structure comprises both a plurality of twisted and interlocked fiber knots and a plurality of thermally bonded fibers.

7. The absorbent article of claim 1, wherein the first fibrous component comprises fibers of a dtex between 1.5 to 1.9.

8. The absorbent article of claim 1, wherein the first fibrous component comprises fibers having a length of between 30 mm to 75 mm.

9. The absorbent article of claim 1, wherein the first fibrous component comprises fibers having a length of between 35 mm to 45 mm.

10. An absorbent article, comprising:
    a topsheet;
    an absorbent core; and
    a secondary topsheet positioned between the topsheet and the absorbent core,
    wherein the secondary topsheet comprises a hydroentangled fibrous structure, the hydroentangled fibrous structure having a basis weight between 35 grams per square meter (gsm) and 65 gsm, the hydroentangled fibrous structure comprising:
    from 30% to 60% by weight of the hydroentangled fibrous structure of a cellulosic fibrous component, fibers of the cellulosic fibrous component having 1.3 to 7.0 dtex;
    from 10% to 25% by weight of the hydroentangled fibrous structure of a non-cellulosic fibrous component; and
    from 35% to 55% by weight of the hydroentangled fibrous structure of a polyolefin-based binder fibrous component, the polyolefin-based binder fibrous component being a bicomponent fiber having a thermally activated binder component,
    wherein the hydroentangled fibrous structure has a machine direction (MD) bending stiffness of 0.2 mN·cm to 7 mN·cm according to EDANA Test Method WSP 090.5 and a rewet value of 0.2 g to 7.0 g according to EDANA Test Method WSP 080.10.

11. The absorbent article of claim 10, wherein the cellulosic fibrous component comprises rayon.

12. The absorbent article of claim 10, wherein the non cellulosic fibrous component comprises polyethylene terephthalate fibers.

13. The absorbent article of claim 12, wherein the polyethylene terephthalate fibers are hollow.

14. The absorbent article of claim 12, wherein the polyethylene terephthalate fibers are spiral shaped.

15. The absorbent article of claim 10, wherein the topsheet comprises an apertured formed film.

16. The absorbent article of claim 10, wherein the fibers of the cellulosic fibrous component have between a 1.5 to 1.9 dtex.

17. The absorbent article of claim 10, wherein the fibers of the cellulosic fibrous component have a length of between 30 mm to 75 mm.

18. The absorbent article of claim 10, wherein the fibers of the cellulosic fibrous component have a length of between 35 mm to 45 mm.

* * * * *